United States Patent [19]

Suzuki et al.

[11] Patent Number: 4,955,237

[45] Date of Patent: Sep. 11, 1990

[54] METHOD AND APPARATUS FOR MEASUREMENT OF IN-SITU HORIZONTAL STRESS BY FREEZING OF THE GROUND IN-SITU

[75] Inventors: Yoshio Suzuki; Munenori Hatanaka; Junryou Ohara; Yorio Makihara, all of Tokyo, Japan

[73] Assignees: Takenaka Corp; Tokyo Soil Research Co., Ltd., Tokyo, Japan

[21] Appl. No.: 362,867

[22] Filed: Jun. 7, 1989

[51] Int. Cl.$^5$ .............................................. G01B 5/00
[52] U.S. Cl. ......................................... 73/784; 73/823
[58] Field of Search ........................... 73/784, 84, 823

[56] References Cited

FOREIGN PATENT DOCUMENTS

| 607879 | 5/1978 | U.S.S.R. | 73/784 |
| 937607 | 6/1982 | U.S.S.R. | 73/784 |

*Primary Examiner*—Jerry W. Myracle
*Attorney, Agent, or Firm*—Ronald P. Kananen

[57] ABSTRACT

A quality undisturbed sample of of cohesionless soil, in which the in-situ state of stress and strain is kept, can be obtained by in-situ freezing of the soil and subsequent removal of the frozen sample for testing. The in-situ horizontal stress in the cohesionless soil can be determined by the thawing the high quality undisturbed sample or, alternately, the frozen hole made in the frozen ground. A test apparatus and procedure for each of the two alternatives adjusts the pressure on the cylindrical sides of the sample or of the cored hole in the ground, to maintain the respective diameter as thawing occurs. The final pressure indicates the horizontal stress. In the case of testing the cylinder-shaped sample removed from the ground, it is loaded axially to reproduce the vertical load conditions at the level in the ground from where it was taken.

14 Claims, 3 Drawing Sheets

METHOD AND APPARATUS FOR MEASUREMENT OF IN-SITU HORIZONTAL STRESS BY FREEZING OF THE GROUND IN-SITU

BACKGROUND OF THE INVENTION

The present invention relates to a test method and a test apparatus used both in the laboratory and in the field for measuring the in-situ horizontal stress of cohesionless soil such as sand and gravel.

SUMMARY OF THE INVENTION

A first object of the present invention is to provide a laboratory test method and test apparatus to measure the in-situ horizontal stress of cohesionless soil. In this laboratory test, the horizontal stress in-situ is measured by the thawing of a frozen, high quality, undisturbed sample of cohesionless soil under a condition of no lateral strain. This high quality undisturbed sample of cohesionless soil, in which the in-situ state of stress and strain is maintained, can be obtained by an in-situ freezing sampling.

A second object of the present invention is to provide a field test method and test apparatus to measure the in-situ horizontal stress of cohesionless soil. In this field test, the horizontal stress in-situ is measured by the thawing of a frozen bored hole under a condition of no lateral strain after installing the test apparatus into the frozen bored hole. The frozen bored hole is made, for instance, by coring the frozen ground.

Another object of the present invention is to provide a series of test methods to measure the in-situ horizontal stress of cohesionless soil. In the first method of testing, the in-situ horizontal stress is measured by the thawing a high quality undisturbed sample obtained by in-situ freezing sampling under a condition of no lateral strain in a laboratory test. In the second method of testing the in-situ lateral stress is measured using a test apparatus installed into the frozen bored hole made by coring the high quality undisturbed sample used in the first method of testing.

Another object of the present invention is to provide a field test method for measuring the Young's modulus of cohesionless soil in-situ in the horizontal direction using a test apparatus which is the same as that used in the field test for measuring the in-situ horizontal stress after the frozen bored hole is fully thawed.

The prediction of the in-situ state of stress in soil is of major importance in a wide variety of geotechnical problems. Although numerous investigators have achieved varying degrees of success in measuring an in-situ state of stress in cohesive soil, it is still not possible to predict exactly the in-situ state of stress in cohesionless soil deposits.

The in-situ freezing sampling method has been recognized as a reliable method for obtaining a high quality undisturbed sample of cohesionless soil. The in-situ state of stress and strain of cohesionless soil can be kept in the sample by this method of sampling without any significant disturbance. The present invention is made based on the fact that the in-situ horizontal stress can be measured by either the thawing of a high quality undisturbed sample obtained by in-situ freezing sampling in a laboratory or the thawing the frozen bored hole in-situ under a condition of no lateral strain.

To achieve the first object, there is provided a laboratory test method of measuring in-situ horizontal stress by the freezing of the ground in-situ, comprising the steps of:

(a) coring a frozen soil column from the ground using a care tube after the ground is frozen in-situ, (b) preparing a test specimen from the frozen soil column by covering, the frozen test specimen with an impermeable flexible rubber membrane and placing the specimen on a pedestal in a cell, then filling the surroundings of the test specimen in the cell with water applying, a stress which is the same as the vertical effective stress at the depth from which the test specimen was cored to the specimen in the axial direction, and allowing the test specimen to thaw under a suitable air pressure in the cell at the initial stage of the test, and (c) since the radial displacement of the test specimen during thawing while it is being loaded in the axial direction results in some movement of the water level in the cell, adjusting the cell pressure to maintain the water level in the cell constant to restrict the radial strain of the test specimen during thawing, the cell pressure at the time when the frozen test specimen is completely thawed indicating the in-situ horizontal stress.

A high quality undisturbed sample of cohesionless soil, in which the in-situ state of stress and strain is kept, can be obtained by in-situ freezing sampling.

There will be a radial strain of this high quality undisturbed sample while it being thawed in the laboratory test apparatus under an axial load which is same as the effective vertical stress at the depth from where the sample was extracted. This radial strain causes some movement of the level of the water in the pressure cell of the test apparatus. The cell pressure is controlled to keep the level of the water in the pressure cell constant, which means that there is no lateral strain on the sample during the thawing.

The cell pressure at the time when the frozen specimen is completely thawed indicates the in-situ horizontal stress of the soil.

The test apparatus used in the above laboratory test method compares the following.

The pressure cell consists of a transparent plastic cylinder, a top plate and a base plate. The pedestal is fixed on the base plate in the center of the cell. The frozen test specimen prepared by the method described above is set on the pedestal. The frozen test specimen is then covered with an impermeable rubber membrane and sealed to the pedestal and top cap. The top cap is connected to an axial loading rod and a load transducer. The cell is filled with water to a level somewhat higher than the top surface of the test specimen. The space above the water in the cell is filled with air. The air pressure supplied from an compressor is adjusted by a regulator and applied to the space in the cell. An inner cell is fixed on the base plate of the pressure cell around the test specimen. A float is placed on the surface of the water in the inner cell. A gap sensor for measuring the vertical movement of the level of the water in the cell is fixed to the wall of the inner cell at a place just below the float. The vertical movement of the float induces a voltage change in the gap sensor. The air pressure in the cell is adjusted to keep the level of the water constant, which means that there is no lateral strain in the test specimen during thawing. This adjustment of the air pressure is provided using a pressure regulator according to the induced voltage change caused by the movement of the level of the water in the cell. Thus the air pressure in the cell at the stage where the frozen test specimen is completely thawed indicates the horizontal stress of the soil in-situ.

To achieve the second object, there is provided a field test method of measuring in-situ horizontal stress by freezing the ground in-situ, is comprising the steps of:

(1) boring a hole in the ground after the ground is frozen in-situ, (2) setting up the test apparatus for measuring the in-situ lateral stress at the ground surface, then joining the apparatus to a rod, so that the test device can be installed in the frozen bored hole at a desired depth by lowering the rod, initially applying a suitable level of air pressure to the water in the rubber balloon of the test apparatus for tightly fitting the rubber balloon to the surface of the frozen bored hole, and (3) controlling the pressure in the rubber balloon to restrict the radial displacement of the frozen bored hole during thawing, so that the pressure in the rubber balloon, when the frozen bored hole is completely thawed indicates the in-situ horizontal stress of the soil.

The in-situ state of stress and strain of cohesionless soil can be retained in a sample obtained by an in-situ freezing sampling method which does not impede the drainage during freezing. The in-situ state of stress and strain will not be affected by a procedure of coring a frozen sample using a core tube as conducted in freezing sampling.

The inner surface of the frozen bored hole made by coring a frozen sample using a core tube is perfectly smooth. The frozen bored hole is allowed to thaw after a test apparatus is installed into it at a depth where the in-situ stress is measured. The air pressure in the test probe is controlled to restrict the radial displacement of the frozen bored hole during thawing.

The in-situ lateral stress of the cohesionless soil can be measured as a value of the pressure in the test apparatus in the bored hole, at the time when the frozen bored hole is totally thawed.

A test apparatus for the field test method mentioned above comprises the following.

A rubber membrane, having nearly the same diameter of the bored hole, is fixed to both ends of the cylindrically-shaped housing. This provides a closed space like a balloon on the circumferential surface of the test apparatus. The rubber balloon is filled with deaired water which is supplied through a delivery pipe connected to an inlet into the inside of the housing. A heater is installed in the balloon keeps the temperature of the water in the rubber balloon constant. A water head pipe is connected to a two-way electro-magnetic valve located at the upper part of the inside of the housing. The upper part of the water head pipe and the differential pressure transducer are connected to the same air pressure supply pipe. A pore water pressure transducer is mounted on the lower surface of the housing.

This test apparatus is installed into the frozen bored hole at the desired depth for testing. The radial displacement of the bored hole during thawing causes a movement of the water level in the water head pipe. The movement of the water level in the pipe is detected by the differential pressure transducer, and then the regulator adjusts the air pressure to maintain the water in the pipe at a constant level. Thus, the frozen bored hole is thawed under a condition of no lateral strain.

The pressure in the rubber balloon measured at the time when the frozen bored hole is completely thawed indicates the in-situ lateral stress in the soil. The lateral effective stress in-situ can be calculated from the measured air pressure in the rubber balloon at the final stage and the pore water pressure measured by pore water pressure transducer mounted on the lower surface of the test apparatus.

The object and features of the method for measuring in-situ the lateral stress of cohesionless soil according to the present invention will become more apparent from the following description taken in conjunction with the accompanying drawings.

DETAILED DESCRIPTION OF THE PREFERRED EMBODIMENT

Figure 1:
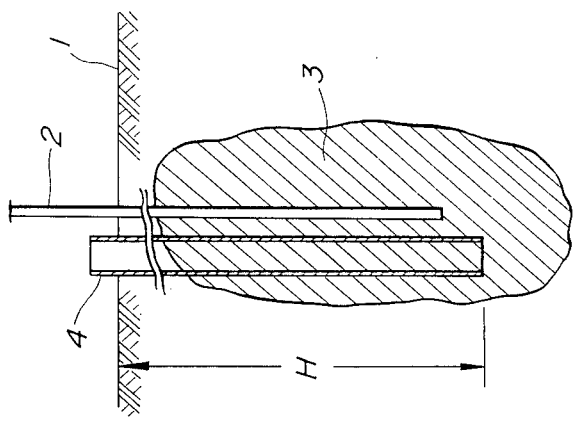
FIG. 1 illustrates the in-situ ground freezing and coring of the frozen ground.

FIG. 1 is a schematic view illustrating a working procedure for freezing the ground and coring the soil column from the frozen ground using a core tube.

In order to measure the in-situ lateral stress at a depth H in a soil deposit 1, a freezing pipe 2 is installed to a desired depth. The surrounding ground including the point H is frozen by supplying the coolant into the freezing pipe. A core-tube 4 is lowered to the depth H in the frozen ground.

A freezing pipe 2, for instance of about 76 mm in its outside diameter, is installed into a bored hole to a depth from which the undisturbed sample is to be obtained.

Liquid nitrogen, a mixture of ethanol and crushed dry ice, or mixture and brine can be used as a coolant for freezing the ground according to the ground condition, cost and time required for freezing the ground.

Because the surrounding area near the freezing pipe, about 20 cm in diameter for the example above, will be disturbed during boring, the undisturbed sample should be cored from the area outside the disturbed area. So, in the case for obtaining gravel sample having a diameter of 30 cm, the diameter of the frozen column would be more than 120 cm. The freezing speed is controlled based on the ground temperature which was monitored using thermo-couples installed in the ground 3. In the case of sand, the diameter of the test specimen usually ranges from 5 cm., to 10 cm, so the diameter of the sand to be frozen in-situ may be about 50 cm.

There are two methods to obtain the frozen soil column from the frozen area 3 in the ground 1. One method is to core the full frozen soil with the freezing pipe 2 from the frozen area 3 using a large diameter steel pipe. After the frozen soil column has been pulled out on the ground surface, the frozen soil column can be cut into small blocks with a suitable size for transportation and cold storage. The test specimen is obtained from the undisturbed area of the frozen soil block using a small core tube for laboratory tests. Another method is to core the frozen soil column from the undisturbed area of the frozen ground 3 using a core tube having a suitably sized inner diameter according to the diameter of the test specimen.

Figure 2:
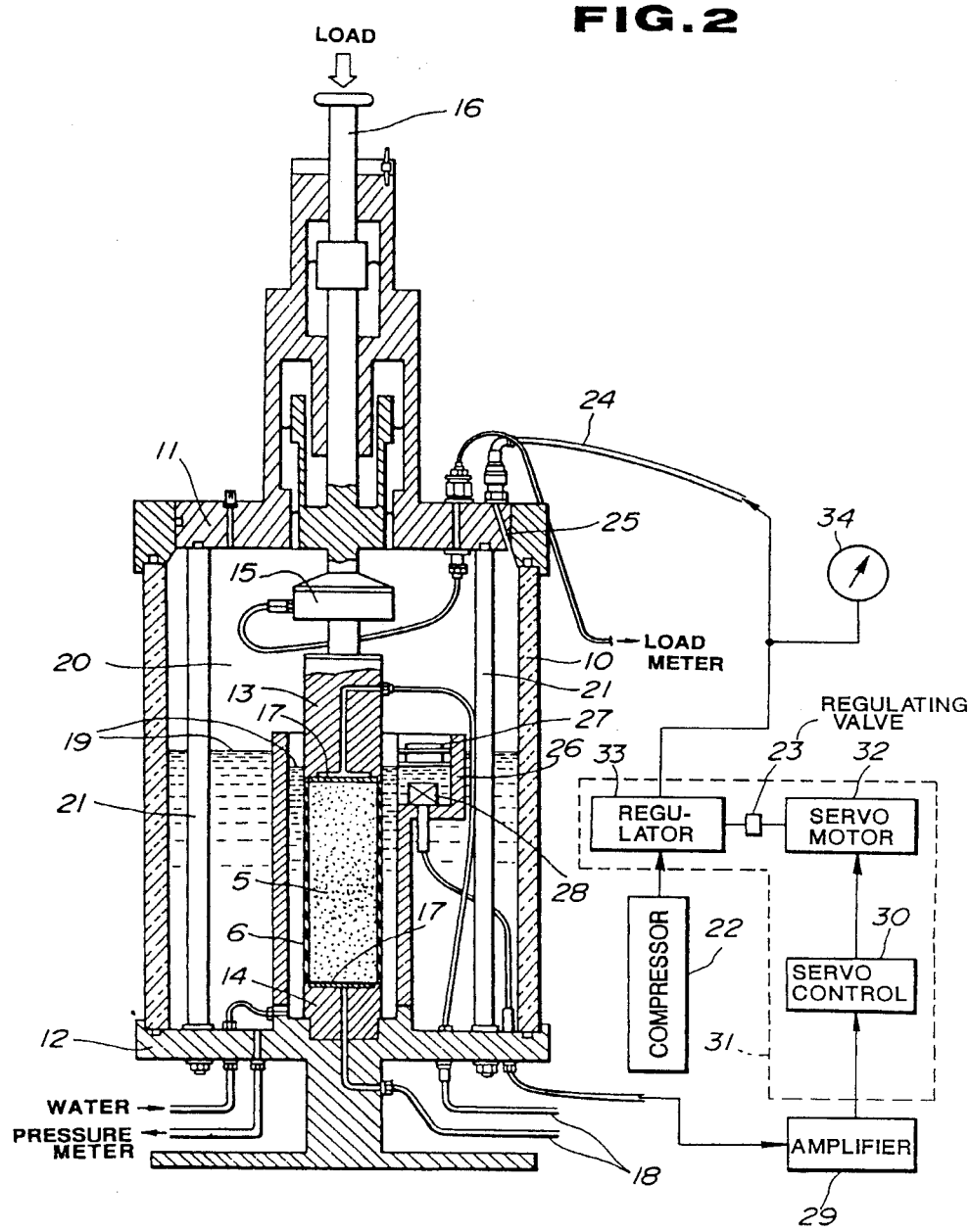
FIG. 2 is a schematic cross-sectional view of the test apparatus for a laboratory test method for measuring the in-situ horizontal stress of cohesionless soil by thawing a frozen test specimen prepared from the high quality undisturbed sample cored from the ground frozen in-situ.

FIG. 2 is a cross sectional view of an apparatus for laboratory tests for measuring the in-situ horizontal stress of cohesionless soil, in which the cylindrical test specimen 5 prepared by the method described above is contained in an impermeable cylindrical rubber membrane 6 which is sealed to a pedestal 14 and top cap 17.

The pressure cell includes a transparent plastic cylinder 10, a top plate 11, and a base plate 12. The top plate 11 and the base plate 12 are connected tightly by three stainless steel bars 21. The frozen test specimen 5 is covered with an impermeable rubber membrane 6 which is sealed to the pedestal 14 and the top cap 13.

The top cap 13 is connected to the loading rod 16 and the axial load transducer 15. The pedestal 14 is fixed on the base plate 12. Porous stone pieces 17 are installed on the surface of the top cap 13 and pedestal 14 at the sides faced to the test specimen. The top cap 13 and the pedestal 14 are connected to the drain pipe 18. The cell is filled with water 19 to a level somewhat higher than the top surface of the test specimen 5. The space 20 above the water 19 in the cell is filled with air. The air pressure supplied from the compressor 22 is adjusted by the regulating valve 23 and applied to the space 20 through plastic tube 24 which is connected to the inlet 25 fixed on the top plate 11. An inner cell 26 is fixed on the base plate 12 in the pressure cell. The float 27 is placed on the surface of the water 19 inside the inner cell 26. The gap sensor 28 for measuring the vertical movement of the water level in the inner cell 26 is fixed just below the float 27 to the inner cell 26. The vertical movement of the level of the water 19 can be indicated by the vertical displacement of the float 27. Vertical displacement of the float 27 induces a voltage change in the gap sensor 28. The induced voltage is amplified by an amplifier 29 and is input to the controller 31. The controller 31 includes the servo controller 30, servo motor 32 and regulator 33 for adjusting the air pressure to keep the level of the water 19 constant. Thus, the lateral strain of the test specimen 5 can be restricted during thawing of the test specimen. The air pressure in the inner cell as measured by the pressure transducer 34 at the stage where the frozen test specimen was completely thawed indicates the lateral stress of the soil in-situ.

The field test method to measure the in-situ horizontal stress of cohesionless soil is performed on a bored hole 7. Such a bored hole 7 is, for instance, prepared by coring the ground after it is frozen by in-situ freezing in the same manner as described above for obtaining a high quality undisturbed sample for the laboratory test described above.

Figure 3:
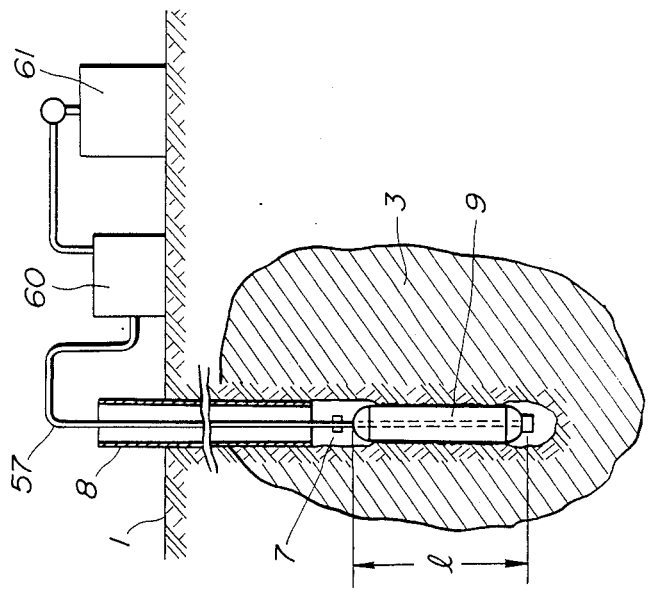
FIG. 3 schematically shows the essentials of the field test to measure the in-situ horizontal stress of the cohesionless soil.

FIG. 3 schematically shows the essentials of the field test to measure the in-situ horizontal stress of the cohesionless soil. A steel pipe 8 is inserted into the bored hole 7 to a depth somewhat shallower than the depth at which the testing is to occur. This serves to keep the inside surface of the hole from collasping. The test apparatus 9, which may be for instance about 60 cm. in length, and has a rubber balloon on its surface, is installed into the bored hole 7 at the depth for testing. Then, a suitable amount of air pressure is applied initially for the fitting of the rubber balloon to the wall surface of the frozen bored hole 7. The testing then occurs during the thawing of the frozen bored hole 7.

Figure 4:
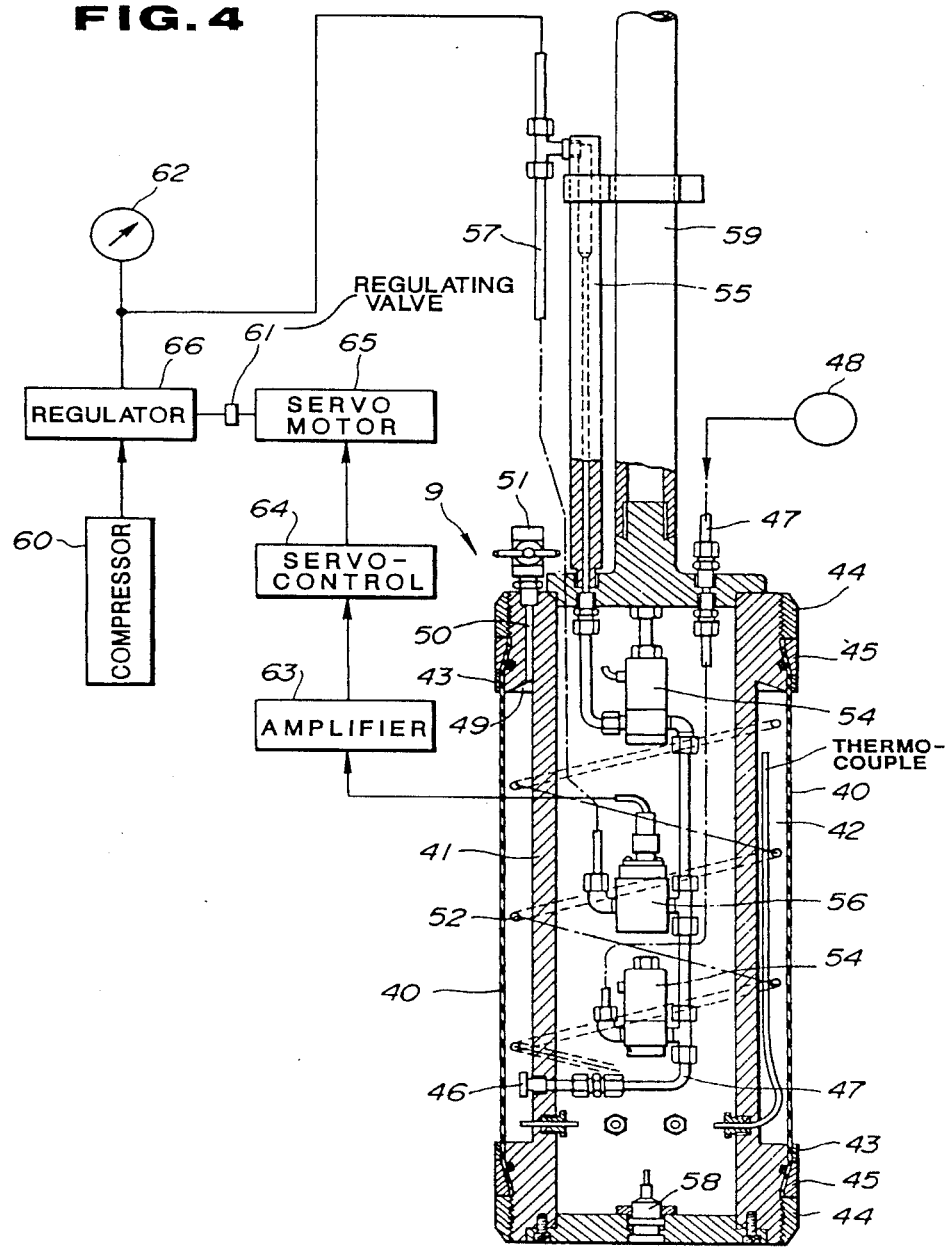
FIG. 4 is a cross section of a test apparatus for the field test.

FIG. 4 is a cross section of the test apparatus for the field test for measuring the in-situ lateral stress of cohesionless soil. A rubber membrane 40, for instance, about 40 cm in length and nearly the same diameter of the bored hole, is fixed to both ends of the cylindrically-shaped housing 41 by the screwing on of the steel ring 44 associated with steel ring 45 and the rubber back-up ring 43 at each end of the test apparatus. As a result, the closed space 42 becomes effectively like the interior of a balloon. The rubber balloon 42 is filled with deaired water. The deaired water is supplied through the pipe 47 which is connected to the inlet 46 attached to the inside of the housing 41. The pipe 47 for supplying water is connected to the water pump 48.

The upper part of 49 of the space 42 is tapered in order to facilitate the saturation of the space 42 with water. Namely, the air in the space 42 can be easily removed via the tapered upper part 49 through a drilled hole 50 and an air valve 51. A coil heater 52 in the space 42 keeps the temperature of the water in the space 42 constant. A water head pipe 55 is connected to a two-way electro-magnetic valve 54 located at the upper part inside of the housing 41. The upper part of the water head pipe 55 and the differential pressure transducer 56 are connected to the same air pressure supply pipe 57. A pore water pressure transducer 58 is mounted on the lower surface of the housing 41.

This test apparatus 9 is attached to the lower end of a rod and is thereby installed at a desired depth for testing. The air pressure from the source 60 is adjusted by the servo motor 65 and supplied to the pipe 47 through the pipe 57. The air pressure can be monitored from the pressure meter 62. The pressure regulator 6 is operated by servo motor 65 and the servo motor regulating valve 61 according to the input from servo controller 64. The input electrical signal to the servo controller 64 is transmitted from the differential pressure transducer 56 and amplified by amplifier 63. The pore water pressure measured from the pressure transducer 58 is used for determination of the effective lateral stress in-situ, which is needed to calculate the coefficient of earth pressure at rest.

After the space 42 is saturated (i.e., filled) with water, the valve 51 is shut, while the device is still on the ground surface. Then the test probe 9 is installed into the frozen bored hole 7 at the depth to be tested. A small pressure is applied to the space 42 to fit the rubber membrane 40 to the inside surface of the frozen bored hole 7. The radial displacement of the bored hole 7 during thawing causes the water level in the water head pipe 55 to rise. The movement of the water level in the pipe 55 will be detected by the differential pressure transducer 56. Then, and then the regulator 61 adjusts the air pressure to maintain the level of the water in the pipe 55 at a constant level, which means that there is no lateral strain (i.e., motion) in the soil while it thaws.

The pressure in the space 42, as monitored by from the pressure meter 62 at the time when the frozen bored hole 3 is completely thawed, indicates the in-situ lateral stress in the soil. The true lateral effective stress in-situ can be calculated from the above monitored air pressure and pore water pressure measured by the pressure transducer 58.

The Young's modulus of cohesionless soil in-situ in the horizontal direction can be measured using the test apparatus which is the same as that used in the field test for measuring the in-situ horizontal stress after the frozen bored hole has been perfectly thawed in the final stage for measuring the in-situ horizontal stress of the field test mentioned above.

The above-detailed description show some examples and devices according to working procedures of the present invention. Many variations and modifications of the present invention will become apparent in actual practice to soil engineers and other skilled workers in the art in possession of the present disclosure, without deviating from the scope of the present invention. The present invention is limited only by the following claims, and not by the above-described examples which are given only for purposes of illustration and are not intended as limiting in any regard.

What is claimed is:

1. A device for indicating the in-situ stress in cohesionless soil, said device comprising
    first means including a flexible member for being placed adjacent a respective surface of a frozen sample, and for establishing an initial contact at positive pressure between said flexible member and said respective surface of said frozen sample,
    second means for controlling said positive pressure between said flexible member and said respective surface of said sample as said sample thaws, in a manner that counteracts and prevents displacement of said flexible member while said sample thaws,
    wherein change of dimension of said sample during said thawing, as indicated by attempted displacement of said respective surface of said sample in a direction normal to the adjacent part of said flexible member as said sample thaws, is prevented by change in said positive pressure during said thawing, and the final value of said positive pressure after said sample is completely thawed is related to the in-situ stress in the soil.

2. The device of claim 1, for the case wherein said frozen sample was obtained by being removed as a vertical cylindrical core from a volume of the soil that was frozen in-situ, said first and second means together comprising
    a cylindrical impermeable rubber membrane as said flexible member, for contacting the respective cylindrical surface of said sample,
    third means for detecting a value corresponding to at least the net average change in position of said membrane at any time during said thawing.

3. The device of claim 2, wherein:
    the axis of said cylindrical membrane is oriented vertically; and
    said third means includes
    a container containing said sample surrounded by said membrane, said container being filled with a liquid to a level above the top of said sample, said container having an open top,
    a float floating in a limited area on the top of said liquid in said container, and
    a gap sensor fixed to the wall of said container beneath said float, for determining the distance from the gap sensor to the float.

4. The device of claim 3, said first means comprising
    a base plate, a top plate, and a cylindrical exterior wall connected at its bottom and top to said base plate and top plate, respectively, to provide a sealed volume, said container being integrally provided with said base plate,
    a top cap and a pedestal in said sealed volume between which said cylindrical sample is held at its upper and lower flat ends, respectively, and loading means for applying a force between said top cap and pedestal, along the axis of said cylindrical sample, corresponding to the vertical pressure on the sample in accordance with its depth in the ground from where it was taken, and
    ports for adjusting the level of said liquid in said container and the pressure of a gas above said liquid,
    wherein the pressure of said gas is adjusted to determine said pressure of said membrane on said cylindrical wall of said sample as it thaws.

5. The device of claim 4, wherein said second means comprises
    an amplifier receiving a signal from said gap sensor indicating change in the distance between said gap sensor and said float,
    a pressurized source of said gas, and
    a regulator connected to said source of gas and to the inside of said sealed volume, for providing said adjustment of the pressure of said gas inside said sealed volume in accordance with said signal from said gap sensor.

6. The device of claim 4, comprising
    said top cap and said pedestal being sealed to respective edges of said flexible membrane,
    said first means further including a porous stone plate between each end on said cylindrical sample and said top cap and pedestal, respectively, and means for draining out of said sealed volume any water from said sample as it thaws.

7. The device of claim 1, for the case wherein said thawing of said frozen sample occurs in-situ, said sample being what remains after a volume of the soil is frozen in-situ and a vertical cylindrical core is removed from the frozen volume, said first and second means together comprising
    a cylindrical impermeable rubber membrane as said flexible member, for contacting the respective cylindrical surface of said sample in-situ,
    third means for indicating a value corresponding to at least the net average change in position of said membrane at any time during said thawing.

8. The device of claim 7, said frist means comprising
    a base part, a top part, and a rigid cylindrical interior wall connected at its bottom and top to said base part and top part, respectively, to provide a sealed annular volume between said membrane and said interior wall, the ends of said cylindrical membrane being connected to said base and top parts, respectively, said base and top parts and cylindrical interior wall providing an interior space extending inside said sealed annular space,
    a first port extending through said top part into said sealed annular space for exhausting gas from said sealed annular space,
    a second port extending through said top part and connected to a third port extending through said interior wall, for filling said sealed annular space with said liquid, and
    a fourth port extending through said top part for providing a reference gas pressure,
    wherein the pressure of said liquid is adjusted to determine said pressure of said membrane on said cylindrical wall of said sample as it thaws.

9. The device of claim 8, said first means comprising
    a differential pressure transducer in said interior space, connected to said third and fourth ports, for comparing said reference gas pressure with said pressure of said liquid in said annular space, and to output a signal as a result of said comparison.

10. The device of claim 9, comprising
a rod connected at a first end to said first means for lowering same into said hole to the position of said sample,
a liquid-head pipe connected at its top end to said gas line and at its lower end to a port through said top part of said first means,
wherein motion of said flexible membrane as said sample thaws causes the level of liquid in said liquid-head pipe to change, thereby changing the reference pressure provided to said differential pressure transducer.

11. The device of claim 7, said first means including a pressure transducer mounted in said bottom part for measuring the pressure of the pore water in said in-situ sample after it thaws.

12. The device of claim 8, wherein said gas is air and said liquid is deaired water.

13. A method for determining the in-situ horizontal stress in cohesionless soil, comprising
obtaining a sample of said soil in which said in-situ stress is stored by freezing a volume of said soil in-situ,
contacting said sample with a flexible membrane with a positive pressure of the contact, while maintaining or reproducing any vertical stress on the sample,
allowing said sample to thaw while detecting any net displacement of said flexible membrane as a result of extension of said sample during thawing in a direction corresponding to said horizontal stress, and
countering any such detected net motion of said flexible membrane during said thawing by increasing the pressure of said contact of said membrane with said sample, to the extent of cancelling any such displacement,
wherein said in-situ horizontal stress is indicated by the final pressure of said flexible membrane on said thawed sample.

14. The method of claim 13, comprising measuring the pressure of pore water at the location in the ground of the sample, and using the value thereof together with the final value for the pressure to determine the value of said in-situ horizontal stress.

* * * * *